(12) United States Patent
Biellak et al.

(10) Patent No.: US 9,404,873 B2
(45) Date of Patent: Aug. 2, 2016

(54) WAFER INSPECTION WITH MULTI-SPOT ILLUMINATION AND MULTIPLE CHANNELS

(71) Applicant: KLA-Tencor Corporation, Milpitas, CA (US)

(72) Inventors: Stephen Biellak, Sunnyvale, CA (US); Mehdi Vaez-Iravani, Los Gatos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 54 days.

(21) Appl. No.: 13/783,290

(22) Filed: Mar. 2, 2013

(65) Prior Publication Data
US 2013/0235374 A1 Sep. 12, 2013

Related U.S. Application Data

(60) Provisional application No. 61/608,798, filed on Mar. 9, 2012.

(51) Int. Cl.
*G01N 21/88* (2006.01)
*G01N 21/95* (2006.01)

(52) U.S. Cl.
CPC ........ *G01N 21/8806* (2013.01); *G01N 21/9501* (2013.01)

(58) Field of Classification Search
CPC ............ G01N 21/9501; G01N 21/956; G01N 21/8806; G01N 21/94; G01N 21/47; G01N 2021/4711; G01N 2021/8864; H01L 22/12; H01L 21/67288; H01L 2924/00; H01L 21/681; G03F 1/84; G03F 7/70025; G02B 27/46
USPC .......... 356/237.5, 237.4, 237.2, 237.1, 237.3, 356/394, 237.6; 382/145, 149, 144, 147, 382/141
See application file for complete search history.

(56) References Cited

U.S. PATENT DOCUMENTS

| 6,201,601 | B1 | 3/2001 | Vaez-Iravani et al. |
| 6,208,411 | B1 * | 3/2001 | Vaez-Iravani ............... 356/237.2 |
| 6,248,988 | B1 * | 6/2001 | Krantz ................. G02B 21/004 250/201.3 |

(Continued)

FOREIGN PATENT DOCUMENTS

| JP | 11-083753 | 3/1999 |
| JP | 2002-195959 | 7/2002 |
| KR | 10-0132435 | 4/1998 |

OTHER PUBLICATIONS http://press.thorlabs.com/articles/video-rate-scanning-confocal-microscopy-and-microendoscopy/protocol/.*

(Continued)

*Primary Examiner* — Tarifur Chowdhury
*Assistant Examiner* — Mohamed K Amara
(74) *Attorney, Agent, or Firm* — Ann Marie Mewherter

(57) ABSTRACT

Systems configured to inspect a wafer are provided. One system includes an illumination subsystem configured to illuminate a set of spots on a wafer and a collection subsystem configured to collect light from the set of spots. The collection subsystem separately images the light collected from each of the individual spots onto only a corresponding first detector of a first detection subsystem. The collection subsystem also images the light collected from at least some of the individual spots onto a number of second detectors of a second detection subsystem that is less than a number of spots in the set. Output produced by the first and second detectors can be used to detect defects on the wafer.

18 Claims, 3 Drawing Sheets

(56) References Cited

U.S. PATENT DOCUMENTS

| | | | |
|---|---|---|---|
| 6,538,730 B2 | 3/2003 | Vaez-Iravani et al. | |
| 6,879,390 B1 * | 4/2005 | Kvamme | G01N 21/8806 356/237.2 |
| 7,075,638 B2 * | 7/2006 | Kvamme | G01N 21/8806 356/237.2 |
| 7,359,045 B2 * | 4/2008 | Some | G01N 21/9501 356/237.2 |
| 7,385,688 B1 | 6/2008 | Kadkly et al. | |
| 7,463,349 B1 | 12/2008 | Biellak et al. | |
| 7,508,504 B2 * | 3/2009 | Jin | G01N 21/4738 356/237.2 |
| 7,671,978 B2 * | 3/2010 | Clark | G01N 21/4738 356/237.1 |
| 7,746,459 B2 * | 6/2010 | Kadkly | G01N 21/9501 356/237.2 |
| 7,990,530 B2 | 8/2011 | Matsui et al. | |
| 8,441,651 B2 * | 5/2013 | Tan | G01N 21/896 356/237.2 |
| 8,755,044 B2 * | 6/2014 | Reich | G01N 21/9501 250/205 |
| 2005/0206886 A1 | 9/2005 | Vaez-Iravani et al. | |
| 2009/0225399 A1 * | 9/2009 | Zhao et al. | 359/298 |

OTHER PUBLICATIONS

International Search Report and Written Opinion for PCT/US2013/029850 mailed on Jun. 27, 2013.

* cited by examiner

WAFER INSPECTION WITH MULTI-SPOT ILLUMINATION AND MULTIPLE CHANNELS

BACKGROUND OF THE INVENTION

1. Field of the Invention

This invention generally relates to systems configured to inspect a wafer.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

In the cases of shot noise limited operation as well as wafer noise limited operation, the achievable signal-to-noise ratio of a surface inspection system, at constant throughput, is known to scale as the square root of the number of illuminating spots on the wafer. For example, when a system with one spot scans a wafer and achieves a signal-to-noise ratio on a particular defect of S, a corresponding system that scans a water with two spots, each of which is half the area of the original spot, can achieve a signal-to-noise ratio of sqrt(2)*S, assuming all other system parameters remain constant.

This advantage argues for enhancement of sensitivity by increasing the number of illuminating spots substantially, by using spatial multiplexing (multiple spots at the same instant in time). Such a technique has been disclosed in patents such as U.S. Pat. No. 7,385,688 issued on Jun. 10, 2008 to Kadkly et al., which is incorporated by reference as if fully set forth herein.

In the case of spatial spot multiplexing or spatial domain multi-spot, the signals from the spots are all generated in time simultaneously or nearly simultaneously. Therefore, in order to separate these optical scattering signals, typically the collecting optics is constructed to separately resolve the scattering from each spot and to direct and/or image each spot onto a separate optical detector such as a photomultiplier tube, photodiode, charge coupled device (CCD), avalanche photodiode (APD), CMOS sensor, etc. For instance, with three incident spots, three separate detectors could be present, with corresponding sets of optics including, but not limited to, lenses, attenuating filters, wavelength selective filters, spatial apertures, and polarizing elements.

Accordingly, it would be advantageous to develop improved systems for multi-spot wafer inspection.

SUMMARY OF THE INVENTION

The following description of various embodiments is not to be construed in any way as limiting the subject matter of the appended claims.

One embodiment relates to a system configured to inspect a wafer. The system includes an illumination subsystem configured to illuminate a set of spots on the wafer. Individual spots within the set are separated spatially from each other on the wafer. The system also includes a collection subsystem configured to collect light from the set of spots on the wafer. In addition, the system includes a first detection subsystem that includes first detectors and a second detection subsystem that includes second detectors. Each of the first detectors corresponds to only one of the individual spots. The collection subsystem is configured to separately image the light collected from each of the individual spots onto only its corresponding first detector. Each of the first detectors generates output responsive to the light imaged thereon. The collection subsystem is also configured to image the light collected from at least some of the individual spots onto a number of the second detectors that is less than a number of the spots in the set. Each of the second detectors generates output responsive to the light imaged thereon. The system further includes a computer subsystem configured to detect defects on the wafer using the output generated by the first detectors and the second detectors. This system may be further configured as described herein.

BRIEF DESCRIPTION OF THE DRAWINGS

Other objects and advantages of the invention will become apparent upon reading the following detailed description and upon reference to the accompanying drawings in which.

Figure 1:
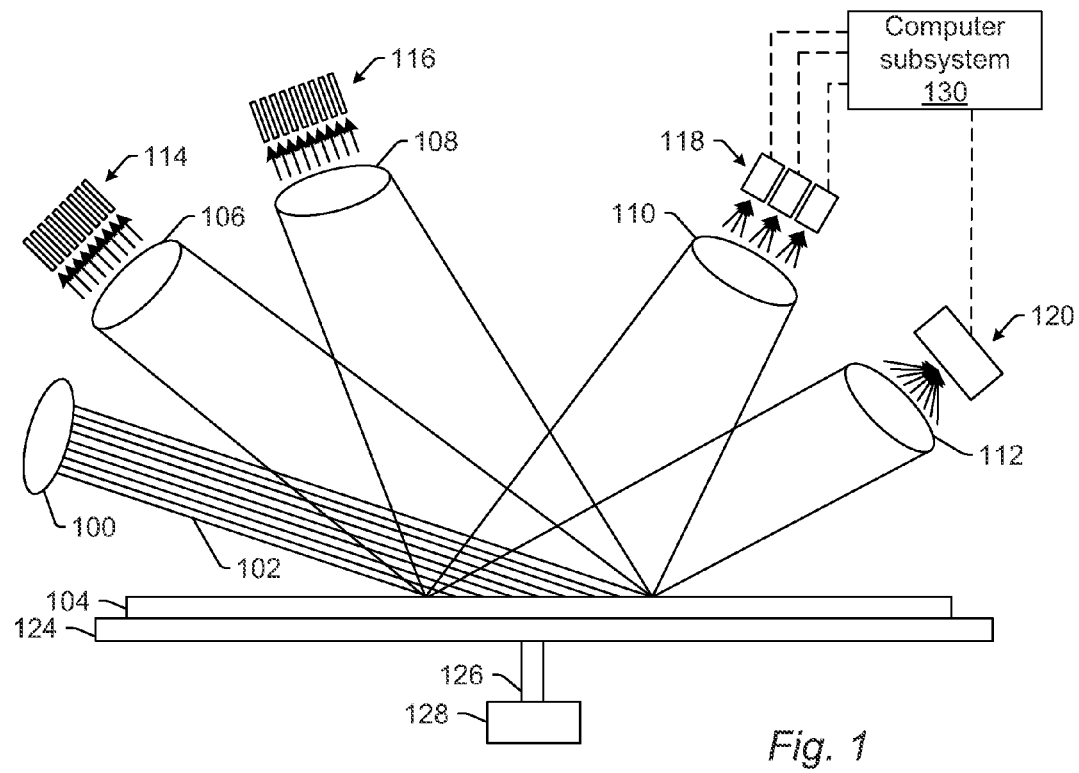
FIG. 1 is a schematic diagram illustrating a side view of one embodiment of a system configured to inspect a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to inspect a wafer. In some currently available inspection systems, multiple collecting channels have been used to separate scatter into various solid angles to improve the signal-to-noise ratio of various defect types of interest. For example, U.S. Pat. No. 6,538,730 issued on Mar. 25, 2003 to Vaez-Iravani et al., which is incorporated by reference as if fully set forth herein, describes two different collection channels referred to as the wide and narrow channels, which function to not only improve signal-to-noise ratio of many defects, but also allow for classification of some defects by means of comparison of the two received signals.

The advantages of multiple collection channels persist in the case of utilizing spatial multi-spot illumination. For instance, with three illuminating spots and the two collectors described above, the scattering signals could be directed simultaneously onto six different detectors. Each individual illumination spot could then provide the same signal-to-noise ratio and classification of every defect encountered as every other illuminating spot.

With larger numbers of simultaneous illuminating spots and more than two collection channels, the number of detectors can become unwieldy. The cost and reliability of such a system, as well as the challenge of matching the performance of each of dozens of channels within a single inspection system and between multiple systems, can potentially become objectionable. It would be advantageous, therefore, to provide an alternate arrangement that maintains the advantages of a multi-illuminating spot, multi-channel inspection system.

One way to accomplish this goal is to first recognize that each collection channel (e.g., a portion of the entire 2*pi solid angle of the collection hemisphere) does not provide equivalent overall benefit to the inspection system user. Some channels improve the signal-to-noise of critical defect types by a factor of ten or more. On the other hand, some other channels, while providing advantages in identifying defect types or shapes, do not necessarily have to provide identical sensitivity. Therefore, one approach is to reduce the number of detectors in a particular collector channel. Several different embodiments configured in accordance with this approach are described herein.

The system includes an illumination subsystem configured to illuminate a set of spots on the wafer. Individual spots within the set are separated spatially from each other on the wafer. In other words, the individual spots preferably do not overlap with one another on the wafer. The illumination subsystem may be configured as described further herein. In this manner, the embodiments described herein may be multi-spot inspection systems.

The system also includes a collection subsystem configured to collect light from the set of spots on the wafer. The collection subsystem may include one or more collectors. For example, as described further herein, the collection subsystem may include two or more collectors, each of which may be configured similarly or differently. Alternatively, the collection subsystem may include only one collector. Each of the one or more collectors may include any suitable refractive optical element(s), any suitable reflective optical element(s), or a combination of refractive optical element(s) and reflective optical element(s). The collection subsystem may be configured to collect light scattered from the set of spots. In this manner, the inspection systems described herein may be dark field inspection systems. The collection subsystem may be further configured as described herein.

The system includes a first detection subsystem that includes first detectors. In one embodiment, the first detectors are not different portions of the same detector. For example, the first detectors may not be different pixels within a single imaging detector. Each of the first detectors generates output (e.g., signals, image signals, data, image data, etc.) responsive to the light imaged thereon. The first detectors may include point or relatively low resolution sensors. The first detectors may also include, for example, discrete photomultiplier tubes (PMTs), charge coupled devices (CCDs), time delay integrators (TDIs), complementary metal-oxide-semiconductor (CMOS) sensors, scientific CMOS's (sCMOS's), PMT arrays, electron-bombarded CCDs (EB-CCDs), electron-multiplying CCDs (EM-CCDs), intensified photodiodes, or avalanche photodiode (APD) arrays.

Each of the first detectors corresponds to only one of the individual spots. In this manner, the number of first detectors included in the first detection subsystem may be equal to the number of individual spots in the set of illuminated spots on the wafer. Therefore, the first detectors and the illuminated spots may have a 1 to 1 correspondence. The collection subsystem is configured to separately image the light collected from each of the individual spots onto only its corresponding first detector. For example, some collectors included in the collection subsystem can spatially separate or resolve the scatter from the multiple spots individually onto separate detectors. In this manner, light from one of the individual spots can be imaged onto only one of the first detectors, light from another of the individual spots can be imaged onto only another of the first detectors, and so on. The first detection subsystem may be further configured as described herein.

The system also includes a second detection subsystem that includes second detectors. In one embodiment, the second detectors are not different portions of the same detector. For example, the second detectors may not be different pixels within a single imaging detector. Each of the second detectors generates output signals, image signals, data, image data, etc.) responsive to the light imaged thereon. The second detectors may be any of the detectors described above. The number of second detectors to included in the second detection subsystem may be different than (e.g., less than) the number of individual spots in the set of illuminated spots on the wafer. Therefore, the second detectors and the illuminated spots may not have a 1 to 1 correspondence. The second detection subsystem may be further configured as described herein.

The collection subsystem is configured to image the light collected from at least some of the individual spots onto a number of the second detectors that is less than a number of the spots in the set. For example, the collection subsystem may include one or more collectors that may spatially separate or resolve scatter from the multiple spots onto fewer detectors than the number of spots.

In one embodiment, the collection subsystem is configured to image the light from at least some of the individual spots onto the second detectors by imaging the light from more than one of the individual spots onto at least one of the second detectors. In this manner, the collection subsystem may be configured to image light from more than one of the individual spots onto a single detector. For example, in one embodiment, each of the second detectors corresponds to only one of two or more subsets of the individual spots, the collection subsystem is configured to separately image the light collected from each of the two or more subsets of the individual spots onto only its corresponding second detector, and at least one of the two or more subsets includes more than one of the individual spots. Therefore, different subsets within the set of spots can be imaged onto different detectors. In some instances, the number of second detectors included in the second detection subsystem may be equal to the number of different subsets of spots.

Each of the subsets may include any number of the individual spots. For example, at least some of the two or more subsets may include different numbers of the individual spots. In one such example, one subset may include two spots that are imaged onto one of the second detectors, another subsystem may include three spots that are imaged onto another of the second detectors, etc. In addition, some of the subsets may include only one of the individual spots. Alternatively, all of the two or more subsets may include the same number of individual spots. For example, each subset may include two individual spots, each subset could include three individual spots, and so on. Each of the individual spots may be included in only one of the subsets. In other words, one individual spot may not be included in more than one subset such that the spots included in any one subset are mutually exclusive from the spots included in any of the other subsets. Each of the individual spots in the set may be included in at least one of the subsets.

However, in some cases, one or more of the individual spots may not be included in any of the subsets. For example, in some embodiments, the collection subsystem is configured to image the light from at least some of the individual spots onto the second detectors by not imaging the light from at least one of the individual spots onto any of the second detectors. In one such example, if there are 10 spots illuminated on a wafer, spots 1-3 can be imaged onto one detector, spots 4-6 can be imaged onto another detector, spots 7-9 can be imaged onto a third detector, and spot 10 may not be imaged onto any of the second detectors of the second detection subsystem (although it may be imaged onto one of the first detectors of the first detection subsystem). In addition, each subset may include only one individual spot, each of which is imaged onto a different one of the second detectors. In this manner, the collection subsystem may image the light from each individual spot onto only its corresponding second detector but not all of the individual spots may be imaged onto a second detector. For example, spot 1 may be imaged onto second detector 1, spot 2 may be imaged onto second detector 2, and spot 3 may not be imaged onto any of the second detectors.

Therefore, one approach is to reduce the number of detectors in a particular collector channel. For instance, with 9 illuminating spots and 4 collection channels, 36 detectors would be required in the most inclusive case. In other words, previous approaches to such a system would suggest 36 detectors to resolve scatter into 4 collection channels from 9 incident spots. However, the inventors have recognized that in some cases fewer detectors are necessary, or even desirable, in some of the collection channels. For example, one could envision a case where one of the collection channels has only three detectors, and a second collection channel has one detector. The collection channel with three detectors could be arranged so that the scattered light from 3 of the 9 spots is imaged on one of the detectors, scattered light from 3 other spots is imaged on a second of the detectors, etc. For a collection channel with only one detector, all 9 of the spots may be imaged on a single detector. For the remaining two collection channels, the scattered light from each of the 9 spots may be imaged on a separate detector, in order to maximize sensitivity to the most relevant defect types. In this case, the number of detectors would be reduced from 36 to 22.

In one embodiment, the collection subsystem includes a first collector coupled to the first detection subsystem and a second collector coupled to the second detection subsystem, the first collector collects the light from the set of spots on the wafer in a first portion of a collection space, and the second collector collects the light from the set of spots on the wafer in a second portion of the collection space different than the first portion of the collection space. Therefore, different collectors can be used for collecting light at different scattering angles. In addition, each collection subsystem may be coupled to only one of the detection subsystems. In one such example, each of the collectors may include a different refractive collector, and each refractive collector may or may not have the same optical design as other refractive collectors included in the system. For example, the optical characteristics of the collectors may vary depending on how the collectors will image the light from the spots onto the detectors of their corresponding detection subsystems. In one embodiment, the first and second portions of the collection space are mutually exclusive. In other words, each of the collectors may not be configured to collect the same scattered light at the same scattering angles as any other collector(s) included in the system. For example, each of the collectors may be positioned in a different area of the collection space of the inspection system. The entire collection space of the system (i.e., the scattering hemisphere) may then be divided up among the collectors, and the collectors in combination may not span the entire collection space.

In one such embodiment shown in FIG. 1, the illumination subsystem described herein may include lens 100 configured to direct light beams 102 to a set of spots on wafer 104 thereby illuminating 9 spots on the wafer. As shown in FIG. 1, the 9 spots may be obliquely incident on the wafer. The collection subsystem may include 4 collectors 106, 108, 110, and 112. The collectors may be further configured as described herein. As shown in FIG. 1, collector 106 may be configured such that scatter from the 9 incident spots is separately imaged by the collection optics channel onto 9 separate detectors 114. Likewise, collector 108 may be configured such that scatter from the 9 incident spots is separately imaged by the collection optics channel onto 9 separate detectors 116. However, collector 110 may be configured such that scatter from the 9 incident spots is imaged by the collection optics channel onto 3 separate detectors 118, and collector 112 may be configured such that scatter from the 9 incident spots is imaged by the collection optics channel onto only one detector 120. The system shown in FIG. 1 may be further configured according to any embodiments described herein.

This concept can be generalized to any number of incident spots, from any of a variety of incident angles, and any number of collector channels. The collection and imaging of multiple scattered light spots onto a single detector can be motivated by both the level of desire for improved defect capture, as described above, as well as a desire to spatially average certain scattered signals generated by the illuminating wafer spots. Therefore, reducing the number of detectors from the maximum that would be needed to separately image every spot in every collection channel would actually provide benefits and advantages for wafer inspection.

In one embodiment, the illumination subsystem is configured to simultaneously illuminate each of the individual spots in the set. In another embodiment, the illumination subsystem is configured to simultaneously and continuously illuminate each of the individual spots in the set. In this manner, the multiple spots may all be incident on the wafer simultaneously and continuously in time.

In some embodiments, the illumination subsystem is configured to illuminate all of the individual spots within the set by directing light to all of the individual spots at the same angle of incidence. In this manner, all of the multiple spots may be incident on the wafer from the same angle. The same angle may be an oblique angle of incidence or a normal angle of incidence and may be "the same" in so far as the capability of the inspection system allows.

Figure 2:
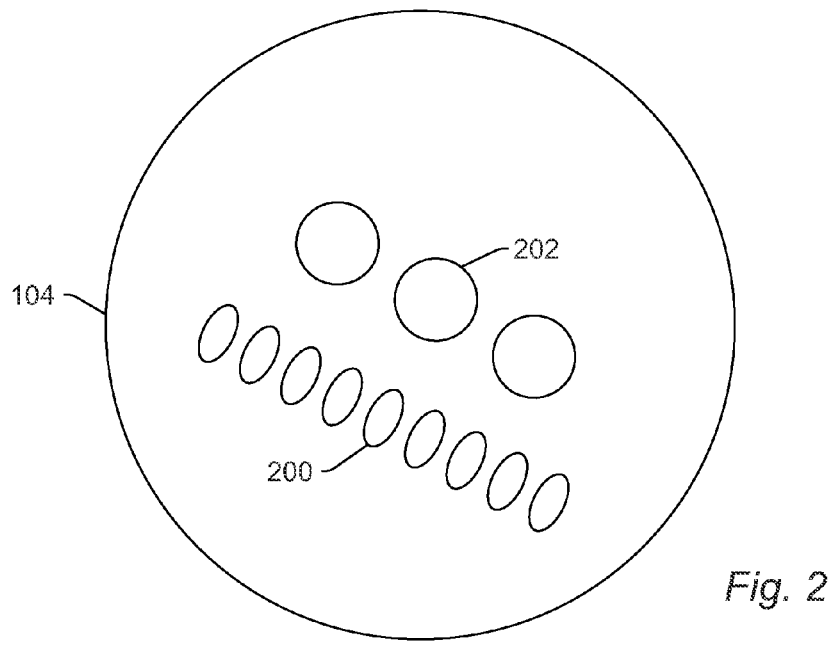
FIG. 2 is a schematic diagram illustrating a plan view of one embodiment of a set of spots illuminated on a wafer.

In another embodiment, the illumination subsystem is configured to illuminate a first portion of the set of spots at a first angle of incidence and a second portion of the set of spots at a second angle of incidence different than the first angle of incidence. In this manner, the multiple spots may be incident on the wafer from different angles (e.g., one oblique angle and one normal angle, two different oblique angles, etc.). In some cases, 7 spots could be incident from one angle of incidence, and 3 spots could be incident from another angle, as described in U.S. Pat. No. 7,463,349 issued on Dec. 9, 2008 to Biellak et al., which is incorporated by reference as if fully set forth herein. For example, as shown in FIG. 2, spots 200 may be incident on wafer 104 from an oblique angle of incidence, and spots 202 could be incident on wafer 104 from a normal angle of incidence. In this manner, the number of spots illuminated on a wafer from one angle of incidence may be different than the number of spots illuminated on the wafer from another angle of incidence.

Figure 3:
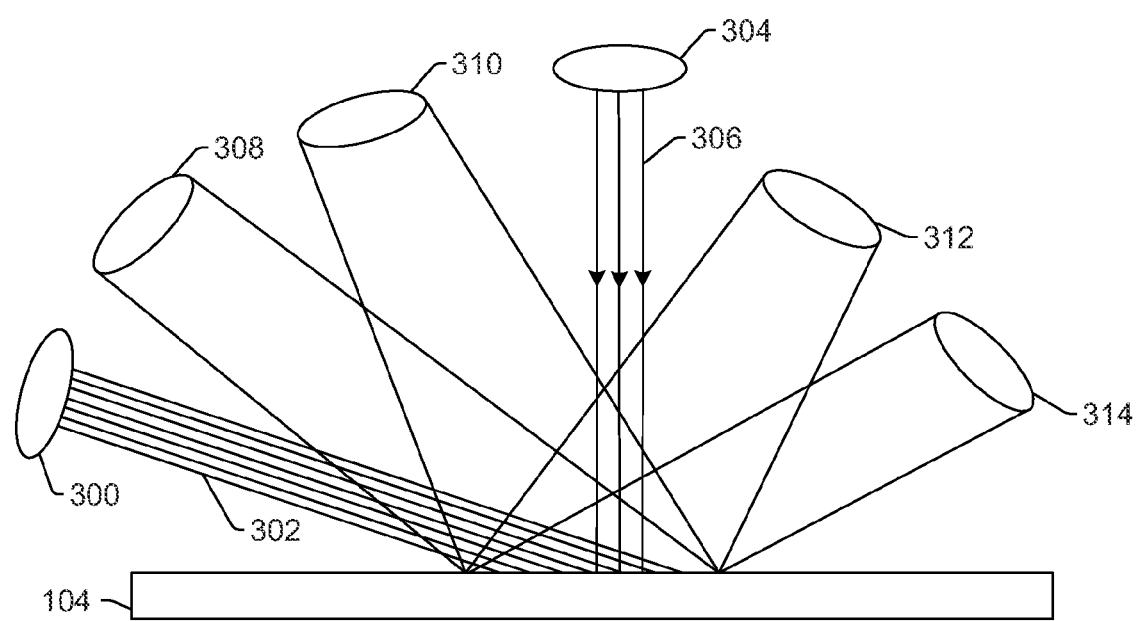
FIG. 3 is a schematic diagram illustrating a side view of one embodiment of a portion of an illumination subsystem and a collection subsystem that may be included in a system configured to inspect a wafer.

In the case of this configuration along with 4 collection channels, 40 detectors would be necessary to separately image every spot in every collection channel. However, if, for the set of three illuminating spots from a second incidence angle, only two of the collectors produce relevant defect capture, the number of detectors could be reduced to 34. For example, in one such embodiment shown in FIG. 3, the illumination subsystem described herein may include lens 300 configured to direct light beams 302 to a set of spots on wafer 104 thereby illuminating 7 spots on the wafer. As shown in FIG. 3, the 7 spots may be obliquely incident on the wafer. The illumination subsystem described herein may also include lens 304 configured to direct light beams 306 to a set of spots on wafer 104 thereby illuminating 3 spots on the wafer. As shown in FIG. 3, the 3 spots may be normally incident on the wafer.

The collection subsystem may include 4 collectors 308, 310, 312, and 314. The collectors may be further configured as described herein. Collector 308 may be configured as collection optics spatially separating scattered light from the 7 obliquely incident spots and 3 normally incident spots onto 10 detectors (not shown in FIG. 3). Likewise, collector 310 may be configured as collection optics spatially separating scattered light from the 7 obliquely incident spots and 3 normally incident spots onto 10 detectors (not shown in FIG. 3). However, collector 312 may be configured as collection optics spatially separating scattered light from the 7 obliquely incident spots onto 7 detectors (not shown in FIG. 3) and not imaging light from any of the normally incident spots onto any detectors. Likewise, collector 314 may be configured as collection optics spatially separating scattered light from the 7 obliquely incident spots onto 7 detectors (not shown in FIG. 3) and not imaging light from any of the normally incident spots onto any detectors. In this manner, the embodiments described herein may use multiple illumination angles and multiple collectors with varying numbers of detectors in each collection channel. The portion of the system shown in FIG. 3 may be further configured according to any embodiments described herein.

One other aspect of the embodiments described herein is the use of time-domain, in conjunction with spatial-domain, spot multiplexing, U.S. Pat. No. 7,990,530 issued on Aug. 2, 2011 to Matsui et al., which is incorporated by reference as if fully set forth herein, describes a system using two or more spots appearing one at a time in periodic intervals. Such an arrangement can be shown to only be effective at increasing sensitivity over the single-spot case when single-spot laser illumination would be limited by laser-induced damage of the inspected surface. Furthermore, the use of this arrangement in conjunction with a continuous-wave (CW) laser, as opposed to a pulsed laser, is problematic.

On the other hand, as described in U.S. Pat. No. 6,201,601 issued on Mar. 13, 2001 to Vaez-Iravani et al., which is incorporated by reference as if fully set forth herein, electro-optic (EO) polarization modulator can be used to direct illumination either at one illumination angle or at a second illumination angle as a selectable function of time. Such an arrangement does not suffer from the expense and mechanical challenge of creating bulk optical delay lines. This arrangement was described at the time as typically generating either one spot at an oblique incident angle or one spot at normal incidence.

In an embodiment, the illumination subsystem is configured to illuminate a first portion of the set of spots in a first time interval and a second portion of the set of spots in a second time interval different than the first time interval. For example, some of the multitude of spots may be incident during one periodic or aperiodic time interval, and some other of the multitude of spots may be incident during another, different periodic or aperiodic time interval. Therefore, different portions of the set of spots may be illuminated at different times such that not more than one portion of the spots is illuminated at any given time. As such, different portions of the spots may illuminate the wafer in sequence at different time intervals that may or may not be periodic. Each of the portions of the spots may include two or more spots. Alternatively, at least one of the portions of the spots may include two or more spots, while some of the portions may include only one spot. In other words, during at least one of the time intervals, multiple spots are illuminated on the wafer.

In one embodiment, the illumination subsystem is configured to illuminate the set of spots by alternating between illumination of one portion of the set of spots and illumination of another portion of the set of spots such that the one portion and the other portion are separated in time. In other words, the illumination subsystem may switch back and forth between different portions of the spots such that some spots are illuminated, then other spots are illuminated, then the first spots are illuminated again, etc. as scanning of the wafer proceeds during inspection. In this manner, the illumination subsystem may not illuminate the wafer with only some spots during one scan or pass and then with other spots during another scan or pass.

The concepts described above can also be extended to multiple spot generation in one illumination angle, and a singular, or, a different number, of spots generated in another illumination angle. Of course, more than two incidence angles can be employed, as well, via, for instance, multiple EO modulators. In some embodiments, the illumination subsystem is configured to illuminate a first portion of the set of spots in a first time interval at a first angle of incidence and a second portion of the set of spots in a second time interval at a second angle of incidence, the first and second time intervals are different from each other, and the first and second angles of incidence are different from each other. In other words, the illumination subsystem may switch back and forth between illumination angles such that at least some of the spots are illuminated at oblique incidence, then at least some of the spots are illuminated at normal incidence, then back to oblique incidence, etc. as scanning of the wafer proceeds during inspection. In this manner, the illumination subsystem may not illuminate at least some spots on the wafer at only one angle of incidence during one scan or pass and then at least some spots on the wafer at a different angle of incidence during another scan.

Figure 4:
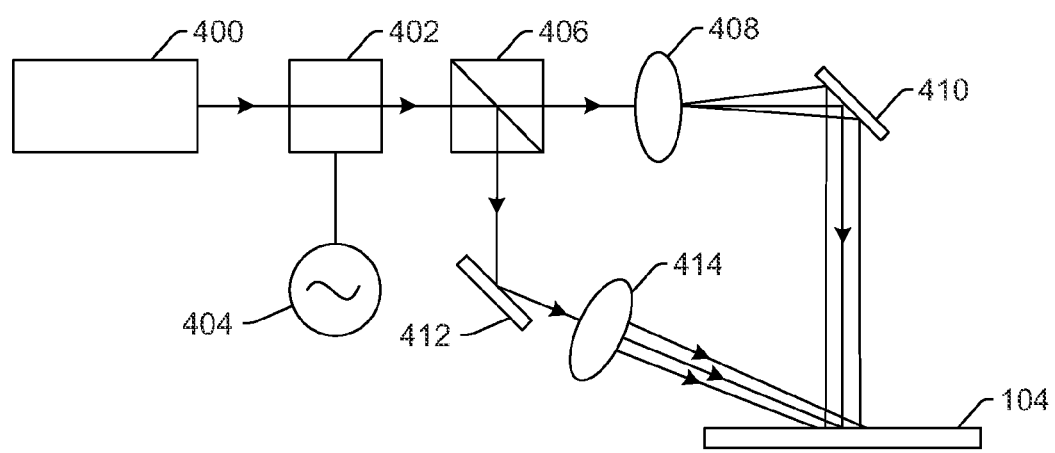
FIGS. 4-5 are schematic diagrams illustrating side views of various embodiments of an illumination subsystem that may be included in a system configured to inspect a wafer.

In one such embodiment for time domain multiplexing with EO modulation and multiple spatial spot generation shown in FIG. 4, the illumination subsystem may include light source 400 such as a laser. Light from the light source is directed to EO polarization modulator 402 that can be used to direct the illumination either at one illumination angle or at a second illumination angle as a selectable function of time. For example, EO modulator 402 is coupled to voltage source 404 and alters the polarization of the light from the light source as a function of time, and light from the EO modulator is directed to polarizing beam splitter 406, which directs light having one polarization along one optical path and light having a different polarization along another optical path.

The multi-spot generation for the different incidence angles can be accomplished by different optical elements, for instance diffractive optical elements (DOEs), in the different incident pathways, after the EO switch. Some spots can be incident on the wafer continuously from a particular angle of incidence, and other spots can alternate between two or more angles of incidence, as a function of time, depending on whether the modulators are activated with a fixed-voltage, or voltage pulses, etc. For example, light transmitted by polarizing beam splitter 406 may be directed to optics 408, which are shown generally in FIG. 4 as a lens but may include any suitable multi-beam generator such as a DOE in combination with one or more other elements such as lenses. The multiple light beams may then be directed to wafer 104 by reflective optical element 410 at a normal angle of incidence. Light reflected by polarizing beam splitter 406 may be directed to reflective optical element 412 that is used to direct the light to optics 414, which although shown generally in FIG. 4 as a lens but may include any suitable multi-beam generator such as a DOE in combination with one or more optical elements such as lenses. The multiple light beams may then be directed to wafer 104 at an oblique angle of incidence. As shown in FIG. 4, 3 spots may be generated for normal incidence and 3 spots may be generated for oblique incidence. However, any suitable number of spots may be generated for normal and oblique incidence (e.g., 5 spots for oblique incidence and 3 spots for normal incidence). The illumination subsystem shown in FIG. 4 and a system that includes such an illumination subsystem may be further configured according to any embodiments described herein.

By using such an arrangement, some detection elements in some collection channels can be employed to detect scattered light generated solely by spots incident at a certain angle, and other detectors in the same, or other collection channels, can be employed to detect scattered light generated by spots incident from different angles, as a function of time. In other words, the processing of some, but not necessarily all, of the detector signals will be linked to the state of the EO switch to distinguish between light incident at time t1 from, say, normal incidence, and light at time t2 incident from, say, oblique incidence. This will allow for the separation and classification of defect types based on their scattering characteristics under illumination from two angles of incidence, as described in the '601 patent referenced above.

The illumination subsystem may also be configured to simultaneously and continuously illuminate a first portion of the set of spots and to periodically or aperiodically illuminate a second portion of the set of spots. In this manner, some spots can be incident on the wafer continuously or simultaneously in time, and other spots can alternate as a function of time as described above (e.g., periodically or aperiodically time). In addition, some spots can be incident on the wafer continuously from a particular angle of incidence, and other spots can alternate between two or more angles of incidence, as a function of time. A large fraction of the available laser power, up to the limit imposed by surface damage considerations, can be employed to be continuously incident in a set of spots on the wafer surface, with an associated set of detectors within a set of solid angle collection channels. The remainder of the laser power can then still be advantageously employed by utilizing the polarization switch and detectors able to time-resolve the scatter from the varied incidence angles.

Figure 5:
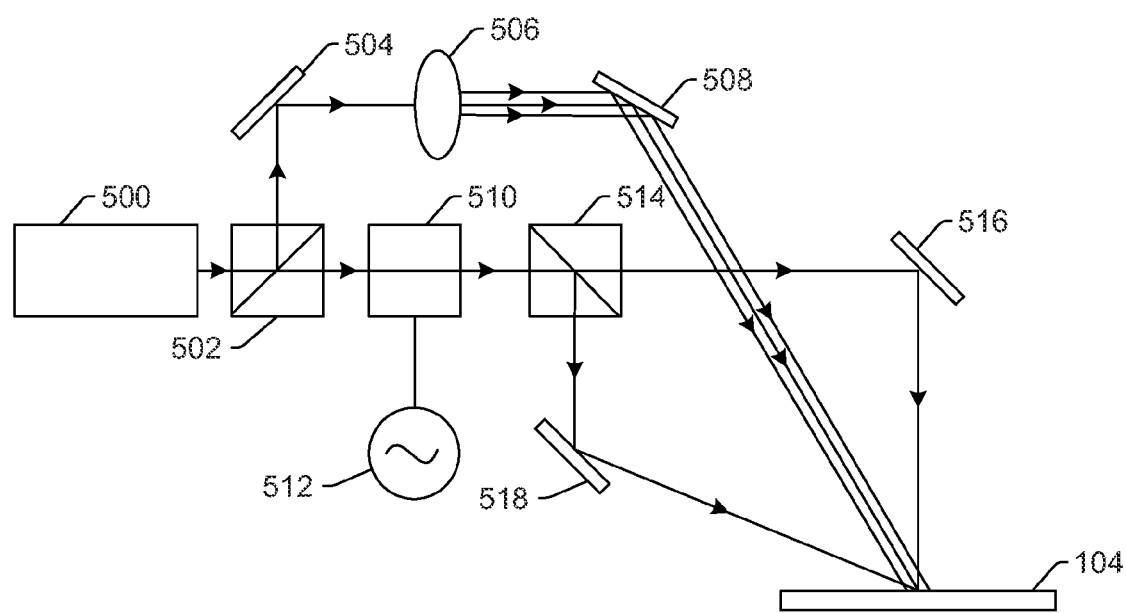

One embodiment of an illumination subsystem that can be used for time domain and spatial domain multiplexing is shown in FIG. 5. For example, as shown in FIG. 5, the illumination subsystem includes light source 500, which may be configured as described herein. Unlike other illumination subsystem configurations described herein, this illumination subsystem includes a beam splitter before the EO modulator. Some spots are therefore generated continuously while other spots can alternate in time between normal incidence and oblique incidence. Light from the light source is directed to beam splitter 502, which reflects a portion of the light to reflective optical element 504. Reflective optical element 504 directs the light to optics 506 shown generally in FIG. 5 as a lens but may include any suitable multi-beam generator such as a DOE in combination with one or more other elements such as lenses. The multiple light beams may then be directed to wafer 104 by reflective optical element 508 at an oblique angle of incidence. Light transmitted by beam splitter 502 is directed to EO polarization modulator 510, which is coupled to voltage source 512 and may be configured as described further herein, and light from the EO polarization modulator is directed to polarizing beam splitter 514, which may be configured as described herein. Light transmitted by polarizing beam splitter 514 may be directed to wafer 104 by reflective optical element 516 at a normal angle of incidence. Light reflected by polarizing beam splitter 514 may be directed to reflective optical element 518 that is used to direct the light to wafer 104 at an oblique angle of incidence. As shown in FIG. 5, 3 spots may be generated for one oblique angle of incidence, 1 spot may be used for another oblique angle of incidence, and 1 spot may be used for normal incidence. However, any suitable number of spots may be generated for normal and oblique incidence. The illumination subsystem shown in FIG. 5 and a system that includes such an illumination subsystem may be further configured according to any embodiments described herein.

In some embodiments, the illumination subsystem is configured to illuminate at least some of the spots in the set discontinuously in time, and at least one of the first and second detectors that detects the light collected from discontinuously illuminated spots in the set is configured to resolve the light as a function of time. For example, some of the scatter collected from some of the time dependent incident spots may be directed onto the same detector and the detector may resolve the origin of the scatter as a function of time.

The system also includes a scanning subsystem configured to scan the set of spots over a surface of the wafer. In this manner, the sample or the spots may be translated in a fashion such that the entire sample can be inspected. As shown in FIG. 1, the scanning subsystem may include chuck 124. The scanning subsystem may also include shaft 126 coupled to chuck 124 and positioning subsystem 128. The positioning subsystem may include various elements such as a motor, gears, stages, and the like that are configured to rotate and/or translate shaft 126. Shaft 126 may be coupled to chuck 124 in such a manner that rotation and/or translation of the shaft causes rotation and/or translation of the chuck and thereby the wafer. The scanning subsystem may translate the wafer, either in a spiral or X-Y fashion, or some combination of the two. Both X-Y serpentine scans and RT-XY hybrid scans may be employed to translate the wafer relative to the illumination and collection optics.

The system further includes a computer subsystem configured to detect defects on the wafer using the output generated by the first detectors and the second detectors. For example, the system shown in FIG. 1 may include computer subsystem 130 coupled to detectors 118 and 120 to receive the output produced by the detectors. The computer subsystem may also be coupled to any other detectors included in the system in a similar manner. The computer subsystem may be configured to detect the defects on the wafer using the output and any suitable defect detection algorithm and/or method. For example, the computer subsystem may apply a defect detection threshold to the output and any output found to be above the defect detection threshold may be identified as a defect or a possible defect.

The computer subsystem may include any suitable computer system known in the art. For example, computer subsystem 130 may take various forms, including a personal computer system, mainframe computer system, workstation, image computer, parallel processor, or any other device known in the art. In general, the term "computer subsystem" may be broadly defined to encompass any device having one or more processors, which executes instructions from a memory medium.

Further modifications and alternative embodiments of various aspects of the invention will be apparent to those skilled in the art in view of this description. For example, systems configured to inspect a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system to inspect a wafer, comprising: an
   illumination subsystem that illuminates a set of spots on the wafer, wherein the illumination subsystem further simultaneously illuminates at least two individual spots in the set of spots on the wafer, and wherein all of the individual spots within the set that are simultaneously illuminated on the wafer are separated spatially from each other on the wafer such that none of the individual spots within the set that are simultaneously illuminated on the wafer overlap with one another on the wafer;
   a collection subsystem that simultaneously collects light from said all individual spots within the set of spots that are simultaneously illuminated on the wafer;
   a first detection subsystem comprising first detectors, wherein each of the first detectors corresponds to only one of the individual spots, wherein the collection subsystem comprises a first collector coupled to the first detection subsystem, wherein the first collector collects the light from the set of spots on the wafer in a first portion of a collection space, wherein the first collector further simultaneously and separately images the light collected from each of the individual spots onto only its corresponding first detector, wherein each of the first detectors generates output responsive to the light imaged thereon, wherein the first detectors are not different portions of the same detector, and Wherein a total number of the first detectors in the first detection subsystem is equal to a total number of the individual spots in the set of spots on the wafer;
   a second detection subsystem comprising second detectors, wherein the collection subsystem further comprises a second collector coupled to the second detection subsystem, wherein the second collector collects the light from the set of spots on the wafer in a second portion of the collection space different than the first portion of the collection space, wherein the first and second collectors have different optical characteristics, wherein the second collector further simultaneously images the light collected from at least two of the individual spots simultaneously illuminated on the wafer and separated spatially from each other on the wafer onto only a single one of the second detectors by imaging the light from more than one of the individual spots simultaneously illuminated on the wafer and separated spatially from each other on the wafer onto only the single one of the second detectors while the first collector simultaneously images the light collected from each of the individual spots simultaneously and separately onto only its corresponding first detector, wherein the light collected from the at least two individual spots overlaps with each other at the detector plane of the single one of the second detectors, wherein each of the second detectors generates output responsive to the light imaged thereon, wherein the second detectors are not different portions of the same detector, wherein the second detectors and the illuminated spots do not have a 1:1 correspondence and wherein a total number of the second detectors in the second detection subsystem is less than the total number of the individual spots in the set of spots of the wafer; and
   a computer subsystem that detects defects on the wafer using the output generated by the first detectors and the second detector.

2. The system of claim 1, wherein the illumination subsystem is further configured to simultaneously illuminate each of the individual spots in the set.

3. The system of claim 1, wherein the illumination subsystem is further configured to simultaneously and continuously illuminate each of the individual spots in the set.

4. The system of claim 1, wherein the illumination subsystem is further configured to illuminate all of the individual spots within the set by directing light to all of the individual spots at the same angle of incidence.

5. The system of claim 1, wherein the illumination subsystem is further configured to illuminate a first portion of the set of spots at a first angle of incidence and a second portion of the set of spots at a second angle of incidence different than the first angle of incidence.

6. The system of claim 1, wherein the illumination subsystem is further configured to illuminate a first portion of the set of spots in a first time interval and a second portion of the set of spots in a second time interval different than the first time interval.

7. The system of claim 1, wherein the illumination subsystem is further configured to illuminate a first portion of the set of spots in a first time interval at a first angle of incidence and a second portion of the set of spots in a second time interval at a second angle of incidence, wherein the first and second time intervals are different from each other, and wherein the first and second angles of incidence are different from each other.

8. The system of claim 1, wherein the illumination subsystem is further configured to illuminate the set of spots by alternating between illumination of one portion of the set of spots and illumination of another portion of the set of spots such that the one portion and the other portion are separated in time.

9. The system of claim 1, wherein the illumination subsystem is further configured to simultaneously and continuously illuminate a first portion of the set of spots and to periodically illuminate a second portion of the set of spots.

10. The system of claim 1, wherein the illumination subsystem is further configured to simultaneously and continuously illuminate a first portion of the set of spots and to aperiodically illuminate a second portion of the set of spots.

11. The system of claim 1, wherein the illumination subsystem is further configured to illuminate at least some of the spots in the set discontinuously in time, and wherein at least one of the first and second detectors that detects the light collected from discontinuously illuminated spots in the set are configured to resolve the light as a function of time.

12. The system of claim 1, wherein each of the second detectors corresponds to only one of two or more subsets of the individual spots, wherein the second collector is further configured to separately image the light collected from each of the two or more subsets of the individual spots onto only its corresponding second detector, and wherein at least one of the two or more subsets comprises more than one of the individual spots.

13. The system of claim 12, wherein at least some of the two or more subsets comprise different numbers of the individual spots.

14. The system of claim 12, wherein all of the two or more subsets comprise the same number of the individual spots.

15. The system of claim 1, wherein the collection subsystem is further configured to not image the light from at least one of the individual spots onto any of the second detectors.

16. The system of claim 1, wherein the collection subsystem is further configured to collect light scattered from the set of spots.

17. The system of claim 1, wherein the first and second portions of the collection space are mutually exclusive.

18. The system of claim 1, further comprising a scanning subsystem configured to scan the set of spots over a surface of the wafer.

\* \* \* \* \*